(12) United States Patent
Soeda et al.

(10) Patent No.: US 6,383,533 B1
(45) Date of Patent: *May 7, 2002

(54) ENZYME-TREATED PROTEIN-CONTAINING FOOD AND METHOD FOR PRODUCING THE SAME

(75) Inventors: Takahiko Soeda, Tokyo; Katsutoshi Yamazaki; Shoji Sakaguchi, both of Kawasaki, all of (JP)

(73) Assignee: Ajinomoto Co., Inc., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/328,435

(22) Filed: Jun. 9, 1999

(30) Foreign Application Priority Data

Jun. 9, 1998 (JP) .......................................... 10-161094

(51) Int. Cl.⁷ ............................................. A23L 3/3571
(52) U.S. Cl. .............................. 426/56; 426/18; 426/32
(58) Field of Search ................................ 435/189–190, 435/228, 193; 426/20, 42, 52, 56, 549, 32, 10, 568, 574

(56) References Cited

U.S. PATENT DOCUMENTS

| | | | |
|---|---|---|---|
| 5,518,742 A | 5/1996 | Soeda et al. .................. 426/63 |
| 5,658,605 A | * 8/1997 | Soeda et al. .................... 426/7 |
| 5,681,598 A | 10/1997 | Kuraishi et al. ............... 426/36 |
| 5,750,498 A | 5/1998 | Soeda et al. .................... 512/4 |
| 5,846,585 A | * 12/1998 | Ohmura et al. ............. 426/241 |
| 5,907,031 A | 5/1999 | Soeda et al. ................ 538/350 |
| 5,968,568 A | * 10/1999 | Kuraishi et al. ............... 426/56 |
| 6,001,398 A | * 12/1999 | Noda et al. ................... 426/59 |
| 6,030,821 A | * 2/2000 | Soeda et al. ................ 435/188 |

FOREIGN PATENT DOCUMENTS

| | | | |
|---|---|---|---|
| JP | 363044866 | * | 2/1988 |
| JP | 407255426 | * | 10/1995 |
| WO | WO 96/22366 | | 7/1996 |

OTHER PUBLICATIONS

Derwent Abstracts, AN 1984–131090, JP 59–066886, Apr. 16, 1984.

Patent Abstracts of Japan, vol. 1998, No. 6, Apr. 30, 1998, JP 10–028516, Feb. 3, 1998.

Patent Abstracts of Japan, vol. 1997, No. 11, Nov. 28, 1997, JP 09–172944, Jul. 8, 1997.

* cited by examiner

*Primary Examiner*—Keith Hendricks
(74) *Attorney, Agent, or Firm*—Oblon, Spivak, McClelland, Maier & Neustadt, P.C.

(57) ABSTRACT

A food containing a protein treated with at least one transglutaminase and at least one oxidoreductase. The presence of the treated protein enhances the quality of the food.

18 Claims, No Drawings

ENZYME-TREATED PROTEIN-CONTAINING FOOD AND METHOD FOR PRODUCING THE SAME

BACKGROUND OF THE INVENTION

1. Field of the Invention

The present invention relates to foods, including food materials and processed food products, which contain a novel enzyme-treated protein, methods for producing the foods, and an enzyme preparation for producing the foods. In the present invention, the enzymes transglutaminase and oxidoreductase are used for protein modification. Optionally, a substrate of an oxidoreductase, a protein partial hydrolysate, milk protein and/or a thiol group-containing material, may be used in the modification, if desired.

The two enzymes may be used during the general production processes of a variety of foods, and the enzymes can also be used in the form of enzyme preparation for the modification of the protein in foods including food materials and processed food products. The enzyme preparation may be used to modify a wide variety of food materials and processed food products containing protein. Such substrates include, for example, wheat flour, fish paste, poultry and cattle meats, soybean protein and egg white, and in processed foods including wheat-processed foods such as bread, noodles and confectionery, fish-processed foods such as fish cake, fried fish cake and baked fish paste in cylindrical shapes (chikuwa), and cattle meat-processed foods such as ham. The enzyme preparation exerts excellent effects on the modification of food materials such as soft wheat, fresh-water fish paste, poultry and cattle meats, soybean protein, and egg white.

2. Discussion of the Background

Many attempts have been made to modify protein-containing food materials. A large amount of research effort has been carried out regarding the modification of the protein in wheat flour for use in breads, noodles, confectionery and cakes.

For example, processes have been proposed, including a process of putting wheat flour in contact to carbonate gas and ethanol at 40° C. or higher (see JP-B-6-36725); a process of recovering gluten with excellent processability for production of processed foods, comprising adding an oxidant and water to wheat flour (see JP-B-6-34682); and a process of modifying wheat to prepare a type of wheat flour suitable for confectionery, comprising adding water at 40 to 500% by weight to wheat and drying then the resulting mixture at a temperature with no occurrence of the modification of the wheat (see JP-B-5-4055).

A process for modifying wheat flour is also proposed by using transglutaminase (abbreviated as TG hereinafter) catalyzing the transfer reaction of the acyl group in the γ-carboxyamide group of a glutamine residue in a peptide. For example, a process for generating wheat flour with excellent texture for cake is proposed, comprising adding a given amount of TG to wheat flour for cake (see JP-A-2-286031), which is for example a process for preparing bread dough with springiness (U.S. Pat. No. 5,279,839). Furthermore, a process for preparing modified wheat flour is proposed, comprising spraying an aqueous enzyme solution to wheat flour after milling, and subsequently heating, drying and grinding the resulting flour (see JP-A-10-56948).

The known processes are excellent in some aspects, but these processes are still unsatisfactory as means for improving the physico-chemical properties of wheat flour, in view of the production aspects, safety profile, and economy. Accordingly, these processes do not overcome the conventional problems in terms of economy, simplicity and functionality.

Among various types of wheat flour, domestic wheat flour has drawbacks in that the physico-chemical properties thereof are poor because of the presence of soft albumen therein, and in that the flour is apparently of a poor color tone due to the ash content therein. These drawbacks have conventionally been barriers for the enlargement of the application of domestic wheat flour. These problems have not yet been completely overcome.

Meanwhile, it has been reported that fish-paste products having the quality of shape retentivity and moldability and with springiness can be prepared from a low-quality fish paste, by using a combination of TG and an alkali earth metal salt (see JP-A-6-113796). Although the shape retentivity and springiness of low-quality fish paste can thereby be improved therein, even the combination cannot give flexible and smooth texture with good bite to the resulting fish-paste products, although these properties are demanded for fish paste products. It has been very difficult to modify low-grade fish pastes with poorer gelation potency and deteriorated colors and flavor, like fish pastes prepared after landing, compared with fish pastes prepared at sea.

Besides the research works so as to overcome the problems regarding sea-water fish, research works have been promoted in China and East Asia to enlarge the applicable range of fresh-water fish of a possible importance as a fishery resource in the near future as food. Compared with fish pastes prepared from sea fish, those prepared from fresh-water fish have low gelation potency; the gelation potency thereof is rapidly lowered (deteriorated) at a temperature zone around 60° C., particularly significantly. In preparing fish paste products from fresh-water fish pastes, therefore, the gelation potency is lowered because these pastes are exposed to temperatures around 60° C. during treatment processes or under heating. Hence, the resulting fish paste products do not have the desired sensory properties when eaten.

For the production of cattle-meat-processed foods, such as ham, bacon and roasted pork, pickles are generally used for the modification of poultry and cattle meats by the following processes; an immersion process of immersing such meats in pickles; an injection process of injecting a pickle into meats; and a process of injecting a pickle into a meat and additionally adding another pickle as a covering pickle to the resulting meat with a tumbler. As well known in the art, pickles are essential for the production of cattle-meat-processed products including ham and bacon. As used herein, the term "pickles" refers to aqueous solutions of salt and brine-mix preparations of color fixatives such as nitrite salts. Current pickles contain sugar, color fixatives such as nicotinamide, absorbate salts, meat quality modifiers such as polyphosphate salts, and seasonings such as glutamic acid. For the purpose of the improvement of water-holding capacity, emulsifiability, texture profiles such as hardness and elasticity as well as binding property, additionally, pickles are now predominant, comprising a blend with extraneous protein materials including egg white, whey protein, sodium caseinate and soybean protein.

When these extraneous protein materials are added to a pickle in too large of an amount, the flavor thereof adds peculiar odor with a different taste to the resulting products, causing severe deterioration of the quality thereof and the viscosity increase of the pickle, so that the pickle can hardly be injected by means of any injector. When these extraneous protein materials are added to a pickle at a too low concentration, the potential effects of the pickle become weak. It cannot be denied that a pickle blended with proteinous materials conventionally used can exert the intended effects only in a limited manner.

So as to overcome the problem, a method has been proposed, comprising injecting a pickle into ham and the like, wherein a ratio of sodium casemate and soybean protein causing the increase of the viscosity of a solution of the pickle is reduced by using TG (see JP-A-7-255426). However, the composition of the pickle definitely defines the quality of the final food products. Thus, each company in the food industry has its own unique blend technique. As such, the modification of the blend ratio or absolute content of an extraneous protein even for the suppression of viscosity increase is so deleterious that the method is very rarely adopted in a practice.

Soybean protein, a very nutritious, economical food material under ready supply, is now drawing considerable attention. Processed food products from fish and cattle meats through the addition thereto of soybean protein have the problem of smooth touch during swallowing and are poor in terms of color and flavor. Various countermeasures have been adopted against these problems, but no satisfactory solution has been found yet.

Egg white is a protein material for use in a diversified range of food processing, having functions for gelation, emulsification and forming ability. Egg white is an excellent proteinous material, but a gel prepared by heating this material, for example, has high springiness, but low visco-elasticity. Additionally, glucose at a content of about 1% in egg white causes color change therein due to the emergence of browning and the gel further lacks smoothness. Accordingly, a process of removing the sugar from egg white at the production process of egg white powder is drawing attention. To solve these problems unique to egg white, attempts have been made to improve the gelation property of egg white by a general means comprising adding protein modifiers including reductive agents and salts, to egg white. Nevertheless, food additives per se are now likely to be shunned and the effects thereof are low. However, various food industrial companies have made attempts to improve the process of removing the sugar in a variety of fashions, but even the improvement brings about only insufficient effects. As has been described above, how to give high visco-elasticity to the heated gel of egg white and how to improve the color are topic issues for the production of egg white powder.

Conventional methods for food binding include for example a method by means of TG and casein (JP-A-6-284867 and JP-A-8-140594) or a method by means of wheat protein. The former is problematic in that bound areas are discriminated on the resulting bound fresh meat blocks, sometimes causing improper appearance. The latter is problematic in that the range of food types which can be bound with the wheat protein is so narrow from the standpoints of taste and flavor that the wheat protein is applicable only to a limited range of utilities. So as to get an enhanced binding strength to prepare preferable appearance with good taste and flavor, furthermore, a binding technique is now demanded.

As has been described above, none of the conventional protein modification methods is satisfactory as a modification method to prepare a modified protein with good gelation potency (satisfactory properties in terms of all of shape retentivity, cohesiveness, water-holding capacity and binding property), as well as with excellent color and flavor.

SUMMARY OF THE INVENTION

It is an object of the invention to provide foods with improved sensory properties.

It is another object of the invention to provides foods which have improved texture, flavor and/or color.

It is also an object of the present invention to provide a method for modifying the protein of a protein-containing food in a simple, economical manner.

The present invention is based, in part on the discovery that protein-containing food materials and various protein-processed food products can be produced to avoid the disadvantages discussed above, by incorporating into the food materials a protein treated with TG and oxidoreductase.

Accordingly, the objects of the present invention, and others, may be accomplished with a food containing a protein treated with at least one transglutaminase and at least one oxidoreductase.

The objects of the invention may also be accomplished with a method for preparing the food by treating a food material containing a protein with at least one transglutaminase and at least one oxidoreductase.

The objects of the invention may also be accomplished with an enzyme preparation comprising at least one transglutaminase and at least one oxidoreductase.

The objects of the invention may also be accomplished with a pickle suitable for processing poultry and cattle meats, comprising at least one transglutaminase and at least one oxidoreductase.

The objects of the invention may also be accomplished with a method for preparing the food by incorporating into a food material a protein treated with at least one transglutaminase and at least one oxidoreductase.

The objects of the invention may also be accomplished with a method of preparing a food containing a protein treated with at least one transglutaminase and at least one oxidoreductase, by contacting a food containing the protein with the enzyme preparation described above.

The objects of the invention may also be accomplished with a method of preparing a food containing a protein treated with at least one transglutaminase and at least one oxidoreductase, comprising contacting a food containing the protein with the pickle described above.

A more complete appreciation of the invention and many of the attendant advantages thereof will be readily obtained as the same becomes better understood by reference to the following detailed description.

DETAILED DESCRIPTION OF THE INVENTION

A feature of the present invention is the modification of food materials, such as wheat flour, fish pastes, poultry and cattle meats, soybean protein and egg white, to dramatically improve various diverse properties of the food materials. Such properties include, for example, smooth touch during swallowing and excellent bite, i.e., texture, as well as color and flavor. These improvements are based on the presence of the protein treated with the TG and oxidoreductase in the food material.

Thus, the invention relates to a food containing a protein treated with at least one transglutaminase and at least one oxidoreductase. The treatment with the two enzymes may be conducted simultaneously or separately. For example, either of the two enzymes is used first for the treatment, followed by the treatment with the other enzyme; otherwise, the two enzymes are alternatively used in repetition for the treatment. Another treatment may be added if necessary, and this is also encompassed within the scope of the invention.

The following embodiments are also encompassed within the scope of the present invention:

1. A food as described above where the protein is further treated in the presence of at least one of the following: a substrate of the oxidoreductase, a protein partial hydrolysate, milk protein and a thiol group-containing material.
2. The food may be a food material or a processed food product.
3. The food where the oxidoreductase comprises at least one member selected from the group consisting of glucose oxidase, absorbate oxidase and catalase.
4. The food where the protein includes at least one member selected from the group consisting of wheat protein, proteins of fish species such as fresh-water fish species, poultry and cattle meats, soybean protein and egg white protein.
5. An enzyme preparation containing transglutaminase (TG) and oxidoreductase or containing a combination thereof.

The enzyme preparation may contain these two enzymes as a mixture; the enzyme preparation may comprise an enzyme preparation containing TG and an enzyme preparation containing oxidoreductase, or may comprise a combination of these enzyme preparations when these enzymes are intended for use in the modification of the same protein. Thus, the enzymes may be separately packaged in the preparation.

The enzyme preparation may be used for modifying the properties of a protein contained in a food material or a processed food product or a protein to be used for a food material or a processed food product. The enzyme preparation may be used as a protein-modifying agent. The enzyme preparation for direct use for protein modification and the enzyme preparation intended for indirect use therefor are both within the scope of the present invention. The enzyme preparation may also be used in a pickle for processing poultry and cattle meats, in particular.

6. A pickle for processing poultry and cattle meats, where the pickle contains at least one of TG and oxidoreductase.

On a solid basis, the pickle may contain TG in preferably about 1 to 1,000 units, more preferably about 5 to 500 units per 100 g of solid in the pickle and contains oxidoreductase preferably about 1 to 1,000 units, more preferably about 5 to 500 units per 100 g of solid in the pickle. The pickle may satisfactorily contain additionally at least one of a substrate of the oxidoreductase, a protein partial hydrolysate, milk protein and a thiol group-containing material, at their amounts each of preferably about 0.01 to 50 g, more preferably about 0.05 to 30 g per 100 g of solid in the pickle.

7. The enzyme solution or the pickle additionally containing at least one of the following: a substrate of the oxidoreductase, a protein partial hydrolysate, milk protein and a thiol group-containing material, as described in (5) or (6) above.

Per one gram of enzyme preparation described in (5) above, at least one of the following: a substrate of the oxidoreductase, a protein partial hydrolysate protein products, milk protein and a thiol group-containing material is used at their amounts each of preferably about 0.001 to 0.9 g, more preferably 0.01 to 0.3 g; if necessary, other additives may satisfactorily be used alike. As described above, these components are in a blend formulation in the same preparation or are in a combination of formulations for the purpose of the modification of the same protein. In a pickle, the components are used at their amounts as described above.

8. The enzyme preparation described in (5) above, where the enzyme preparation contains TG of about 0.01 to 1,000 units, preferably about 0.1 to 500 units and oxidoreductase of about 0.01 to 1,000 units, preferably about 0.1 to 500 units, per gram of the enzyme preparation.
9. A method for preparing a protein-containing food, comprising a treatment step with TG and oxidoreductase.

The two enzymes, i.e., TG and oxidoreductase, may be used at the following units per g of protein to be treated; TG at about 0.01 to 200 units, preferably about 0.1 to 100 units, and oxidoreductase at about 0.01 to 200 units, preferably about 0.1 to 100 units. At least one of a substrate of the oxidoreductase, a protein partial hydrolysate, milk protein and a thiol group-containing material is used at about 0.0001 to 0.9 g, preferably about 0.001 to 0.3 g, when the two enzymes are used at the amounts described above.

10. The method described in (9) above, where the treatment step with TG and oxidoreductase is conducted by contacting or adding the enzyme preparation in (5) or the pickle in (6) above to a protein-containing food.

For use, the enzyme preparation may be added to exert the activities in the form of an enzyme mixture of the two or in the enzyme mixture with further addition of other compounds (e.g., a substrate of the oxidoreductase, a protein partial hydrolysate, milk protein and a thiol group-containing material) intended for concurrent use, other than the two enzymes. Additionally, the two enzyme components may be separately added one by one or the two enzyme components and other components for the- treatment are separately or simultaneously added to exert their activities. These methods are also encompassed within the scope of the invention.

11. The method described in (9) above, where the treatment process with transglutaminase and oxidoreductase is included in any of the tempering process of milling, a process of preparing fish paste (for example, paste of fresh-water fish), a process of preparing soybean protein, a process of preparing egg white and a treatment process of poultry and cattle meats (immersion and injection process).

Finally, modified wheat flour and processed food products thereof, modified fish paste and processed food products thereof, modified soybean protein and processed food products thereof, modified egg white and processed food products thereof and modified poultry and cattle meats and processed food products thereof can be produced.

12. An enzyme preparation containing TG or oxidoreductase and for executing a modification treatment of a protein, when used concurrently with oxidoreductase or TG.

Because the oxidoreductase serves as a chemical agent to promote the effects of TG on the functional modification, in particular, the oxidoreductase-containing enzyme preparation can be designated as an auxiliary agent of TG for protein modification. The TG-containing enzyme preparation can also effectively work for protein modification, when used concurrently with the oxidoreductase.

The invention is characteristic in that the treatment with two enzymes can treat and modify protein; for practicing the invention, the enzyme preparation of the present invention is effectively used in a simple manner. The enzyme preparation is one preferable, typical example of the invention and is mainly described below. But the invention is not limited thereto.

The enzyme preparation of the present invention is a formulation containing TG and oxidoreductase and serves for protein modification; the enzyme preparation preferably contains at least one of a substrate of the oxidoreductase, a protein partial hydrolysate, milk protein and a thiol group-containing material, and may additionally contain food excipients, if necessary, and various other additives, if necessary.

These enzymes and components are mixed together and contained in one preparation, but these are in a formulation of a combination thereof or in formulations of separate combinations thereof. Furthermore, preparations containing separately two enzymes or a preparation containing a combination of the two enzymes is included as a modification-promoting agent or a modification-supplementing agent within the scope of the invention, when the preparations or the preparation is for the same purpose of protein modification.

The enzyme preparation of the present invention contains TG of about 0.01 to 1,000 units per g of enzyme preparation. Below 0.01 unit in the enzyme preparation, the crosslinking ability of TG is too low enough to modify protein. Above 1,000 units, alternatively, the crosslinking reaction progresses excessively so that the texture of the resulting processed food products gets fragile, with the resultant poor texture during swallowing.

In accordance with the invention, use is made of TG as an enzyme catalyzing the transfer reaction of the acyl group in the y-carboxyamide group in the glutamine residue in the peptide chain of protein. When TG reacts with c-amino group in the lysine residue in a protein as an acyl receptor, $\epsilon(\gamma$-Glu)-Lys bonds are formed within the molecule of the protein or between the molecules. The crosslinking bonds promote crosslinking polymerization of the protein in wheat flour or fish paste, so that a material with characteristic properties including gelation potency, high viscosity and great waterholding capacity, can be recovered.

Any TG can be used in accordance with the invention, as long as the TG has a transglutaminase activity; as the TG, therefore, known TGs may be used (see JP-B-1-50382, incorporated herein by reference). TG from a microbial origin is preferable because the TG does not require Ca for the exertion of the activity thereof. For example, a known TG derived from a microorganism has these properties (see JP-A-64-27471, incorporated herein by reference).

TG is divided into calcium-independent and calcium-dependent types. Either can be used in the present invention. Examples of the former include those derived from microorganisms such as Actinomycetes, *Bacillus subtilis* and the like (see, for example, JP-A-64-27471). Examples of the latter include TG derived from guinea pig liver (see, for example, JP-B-1-50382, incorporated herein by reference), TG derived from microorganisms such as Oomycetes, those derived from animals such as bovine blood, swine blood and the like, TG derived from fishes such as salmon, red sea bream and the like (see, for example, Seki Nobuo et al., Nippon Suisan Gakkaishi, vol.56, No.1, pp.125132 (1990), each incorporated herein by reference), TG derived from oyster, and so forth. Also, TG produced by methods of genetic engineering (see, for example, JP-A-1-300889, JP-A-6-225775, JP-A-7-23737, each incorporated herein by reference) may be used. In accordance with the present invention, any of these transglutaminases can be used, with no specific limitation on the origin and the preparation. However, in view of the function and the economics in the food applications, the calcium-independent transglutaminases are preferable. For example, the transglutaminases derived from microorganisms (JP-A-64-27471, mentioned above) and are preferred enzymes.

The activity unit of TG for use in accordance with the invention is assayed and defined as follows. More specifically, TG is allowed to react with substrates benzyloxycarbonyl-L-glutaminylglycine and hydroxylamine to generate hydroxamic acid, which is then converted to an iron complex in the presence of trichloroacetic acid, to assay the quantity of the iron complex as the absorbence at 525 nm. Using the quantity of hydroxamic acid assayed in such manner, a standard curve is prepared; the quantity of the enzyme generating 1 μmol hydroxamate per minute is defined as one unit of the TG activity unit. The assay is described in detail in JP-A-64-27471, incorporated herein by reference.

Various enzymes may be candidates for the use in combination with TG, but oxidoreductase is effective for overcoming the problems discussed above.

As the oxidoreductase, for example, glucose oxidase, absorbate oxidase, catalase, polyphenol oxidase, peroxidase, dehydrogenase and reductase may be used. From the aspect of supply, economy, safety profile and functionality for foods, in particular, glucose oxidase, absorbate oxidase or catalase are used preferably or reductase in the present invention.

The oxidoreductase is contained at about 0.01 to 1,000 units per gram of the enzyme preparation of the present invention. Below 0.01 unit per gram of the enzyme preparation, the activity of the enzyme is too low so that the effect cannot be exerted. Above 1,000 units, alternatively, the modification effect is not any more enhanced, disadvantageously uneconomically, even if the amount of the enzyme preparation is increasingly added. Enzymes for general use in food processing such as amylase, xylase, hemicellulase, pentosanase, lipoxydase and lipase, other than the oxidoreductase, may serve as the structural components of the enzyme preparation of the present invention; proteases may satisfactorily be used in combination, within a range with no suppression of TG or the oxidoreductase contained in the enzyme preparation of the present invention.

The activity assay of the oxidoreductase varies depending on the enzyme species, but generally, glucose oxidase can be assayed by determining gluconic acid generated through the enzyme reaction; and absorbate oxidase can be assayed by determining dehydroascorbic acid generated through the enzyme reaction. One unit of glucose oxidase is defined as the enzyme quantity oxidizing 1 μmol glucose per one minute at 40° C. and pH 7.0 to generate gluconic acid.

It is preferable to concurrently use at least one of a substrate of the oxidoreductase, a protein partial hydrolysate, milk protein and a thiol group-containing material, from the aspect of improving the functions of TG.

Examples of the substrate of oxidoreductase include β-D-glucose or FAD when glucose oxidase is used, ascorbic acid and its salts when absorbate oxidase is used, and hydrogen peroxide when catalase is used, and so on. Each oxidoreductase catalyses its own specific reaction, and its own substrate takes part in the reaction. A substrate suitable for the oxidoreductase used in the invention is selected. The substrate is used at an amount of about 0.0001 to 0.9 g, preferably 0.001 to 0.3 g, as the total with the following protein partial hydrolysate, milk protein and a thiol group-containing material. When none of the protein partial hydrolysate, milk protein and thiol group-containing material is used, the substrate is singly used at the amount described above.

Examples of the protein partial hydrolysate include a wheat flour protein partial hydrolysate, a milk protein partial hydrolysate, a soybean protein partial hydrolysate and a gelatin partial hydrolysate. These are produced by hydrolysis of the individual proteins by enzymes or acids or alkalis, with no specific limitation, as long as the enzymes or acids or alkalis can meet the objects of the invention. Because commercially available peptides such as lysine peptide have effects similar to those of the protein partial hydrolysate described above, peptides composed of any single amino acid, such as lysine peptide, are also included in the protein partial hydrolysate in accordance with the invention. The protein partial hydrolysate for use in accordance with the invention may have a mean molecular weight of about 600 to 80,000, preferably 1,000 to 20,000.

The protein partial hydrolysate is used at an amount of about 0.0001 to 0.9 g, preferably 0.001 to 0.3 g per g of enzyme preparation, as the total with a substrate of the oxidoreductase, milk protein and a thiol group-containing material.

Casein salts, such as sodium caseinate and calcium caseinate are used as the milk protein, preferably from the respect of the solubility, but caseins containing acid casein and milk whey protein may also be used.

The milk protein is used at an amount of about 0.001 to 0.9 g, preferably 0.01 to 0.3 g as the total with the protein partial hydrolysate and a thiol group-containing material.

Examples of the thiol group-containing material include glutathione and cysteine; yeast extract containing a high concentration of glutathione is practically preferable in view of economy, functionality, rules over food additives, shelf life, and taste and flavor, compared with the remaining substances. Furthermore, the thiol group-containing material additionally have functions to allow TG to exert its activity and stably retain the activity.

The thiol group-containing material is used at an amount of about 0.001 to 0.9 g, preferably 0.01 to 0.3 g, per gram of the enzyme preparation, as the total with the aforementioned three components such as a substrate of oxidoreductase.

As has been described above, food excipients can be used in the enzyme preparation of the present invention. As the excipients, general food excipients are used, including for example saccharides, starches, protein, and thickening polysaccharides. Examples of the saccharides include monosaccharides such as glucose, disaccharides such as lactose and sucrose, oligosaccharides, dextrins, and sugar alcohols such as sorbitol. The starches include various carbohydrates and hydrolyzed starch; and the protein includes soybean protein, milk protein, skim milk, wheat protein, egg white, and plasma protein. Herein, care should be taken when such protein is used, because protein serves as a substrate for TG.

The method of the producing the food according to the present invention is described below.

The inventive method provides a modified protein via treatment of a protein with TG and oxidoreductase, or for producing diverse protein-containing food products such as processed foods, if necessary. These enzymes can be used simultaneously or separately. Within the scope of the objects of the present invention, another treatment may be effected, including the treatment with at least one of a protein partial hydrolysate, milk protein and a thiol group-containing material and other treatments. TG is used according to conventional methods for treatment with TG.

For the enzyme treatment, the enzyme preparation of the present invention is advantageously used in a simple manner. Then, the method for modifying a food material rob such as wheat flour fish paste, poultry and cattle meats, and soybean protein, by using the enzyme preparation of the present invention, will now be described. The treatment method by using the enzyme preparation is just one example of the method for treatment with TG and oxidoreductase, in accordance with the invention. Accordingly, the invention is not limited thereto.

As an example, the use of wheat is described. As well known, wheat is milled by a method comprising grinding wheat grain and separating the shell fraction from the resulting pulverized wheat grain powder, because wheat grain has hard outer shell with fragile and readily break albumen and with a longitudinal groove at the core part of the grain.

The milling process is summarized and described as follows (see for example General Food Industry Dictionary, New Edition, issued by Korin, Co., 1993).

1. Fractionation

A process of removing contaminants such as small stone pieces and the like. Because the removal of impurities is very hard from the final product wheat flour, the raw material wheat is preferably fractionated very carefully.

2. Tempering and Blending

For the purpose of allowing the albumen readily separable by making the shell more hard and for the purpose of allowing the albumen to be softened and be thereby ground readily, water is added to wheat grain, which is then aged for one to two days through nights for tempering. If necessary, additionally, wheat grain types separately tempered as raw materials are blended together at a ratio, depending on the purpose.

3. Milling

From the tempered wheat is separated the shell as much as possible by means of break roll, to recover the albumen in coarse grains (disruption process). Then, the coarse grains are fractionated in size and fed into a purifier, where the contaminated debris of the shell is removed by means of sieving and air fractionation (purification process). Furthermore, the purified coarse grains are ground by means of smooth roll (on smooth face or coarse face), which are then sieved on the basis of powder grain size (grinding process).

4. Recovery of Wheat Flour

Sieved wheat flour fractions of various particle sizes (finished flours) are blended together at a ratio, in conformity with the quality and grade of an objective wheat flour type.

5. Final Process

Thorough mixing for preparing a final product. For supplement, vitamins and the like are mixed with the flour at this process.

For use, the enzyme preparation of the present invention is mixed with milled wheat flour after addition of water thereto, or the enzyme preparation is added to wheat grain at the milling process. The enzyme preparation of the present invention can exert the effects more efficiently, when the enzyme preparation is added at the milling process. In that case, the treatment with at least one of TG, oxidoreductase, a protein partial hydrolysate, milk protein and a thiol group-containing material is particularly preferably executed at a tempering process as described below.

At a tempering process after the fractionation of the raw material wheat grain, TG and oxidoreductase are added, within the range of the amounts thereof to be added, to water, along with if necessary, a protein partial hydrolysate (for example, a wheat protein partial hydrolysate, and a milk protein partial hydrolysate) and/or milk protein and/or a thiol group-containing material, at the timing of water addition during tempering. The amount of water then is with not any specific limitation; water should be added to a final water content in wheat flour to about 14 to 16%, starting from the general water content of ca. 9 to 14% in wheat flour. Subsequently, tempering is effected in a tank for 16 to 50 hours, for passing TG and the oxidoreductase and the like from the surface of wheat grain through wheat germ to allow these enzymes and the like to infiltrate into the inside thereof. The albumen is readily ground through tempering, while the surface shell absorbs appropriate moisture and is hardened owing to the TG action, so that the shell turns fragile and readily breaks. Additionally, the gluten inside the albumen is crosslinked and polymerized together through the TG action, so that springiness is imparted to the resulting wheat flour.

After the tempering process, these processes may be conducted as follows.

Tempered wheat grain is subjected to a water addition process, one to 3 hours prior to the grinding process. As in the processing method at the tempering process, the processing method then comprises uniformly spray coating water dissolving therein at least one of TG, a substrate of the oxidoreductase, a protein partial hydrolysate, milk protein and a thiol group-containing material, over the wheat grain. The processes after the tempering and grinding processes are executed in the same manner as in general wheat processing processes.

For the modification of wheat flour, TG is added at an amount of about 0.01 to 200 units per gram of the protein in wheat. The addition of TG below 0.01 unit gives poor effect on the improvement of the gelation potency; above 200 units, the enzyme reaction proceeds too excessively, so that when bread for example is prepared at such amount of TG, the resulting bread is hardened too much because of the suppression of the expansion, with the resultant improper appearance or texture. Preferably, oxidoreductase is added at an amount of about 0.01 to 200 units per g of the protein in wheat. Below 0.01 unit, the effect of the oxidoreductase over the modification of the color and flavor of wheat flour can hardly be exerted; an amount above 200 units is not preferable, from the standpoint of flavor. At least one of a substrate of the oxidoreductase, a protein partial hydrolysate, milk protein and a thiol group-containing material is added at an amount of about 0.0001 to 0.9 g per gram of the protein in wheat. Below 0.0001 g, noodles prepared by using the resulting wheat flour cannot get improved resilience or springiness; above 0.9 g, noodles prepared by using the resulting wheat flour are fragile with no viscosity, with the resultant inappropriate texture. For the modification of wheat flour, furthermore, the food excipients may satisfactorily be blended to the wheat flour.

When TG and the oxidoreductase are not used in an enzyme preparation form with at least one of a substrate of the oxidoreductase, a protein partial hydrolysate, milk protein and a thiol group-containing material, in accordance with the method of the present invention using the two types of the enzymes, these components may be used nearly simultaneously in the same way as the above-mentioned enzyme preparation is used, or independently, to exert their individual actions. If necessary, the individual components may independently be used in a divided manner at various stages or some multiple components can be used in a repetitive manner or can be used alternatively. Any of these methods using these components are within the scope of the invention. The description above for using the enzymes and the is remaining other components is also applicable to the treatment of fish paste and other food materials, other than wheat protein, as described below.

Wheat flour is divided in the following types: hardwheat flour, semi hard-wheat flour, medium hard-wheat flour, soft-wheat flour and durum semolina flour, and all of these wheat flours may be modified according to the present invention.

The resulting wheat flour modified through the action of TG and the oxidoreductase at the milling process is superior from various standpoints, as compared to the wheat flour modified after milling (JP-A-2-28603 1) and the wheat flour according to U.S. Pat. No. 5,279,839 (see JP-A-10-56948).

Processed food products prepared by using as a food material the modified wheat flour recovered in accordance with the invention may be prepared as described below.

According to conventional methods for producing wheat flour-processed food products, except for using the modified wheat flour of the present invention as the wheat flour, wheat-processed food materials can be prepared from a raw material the enzyme treated wheat flour recovered in accordance with the invention.

For the preparation of a loaf of bread, for example, the modified wheat flour recovered in accordance with the invention is mixed with yeast, yeast food and water by means of a mixer. Subsequently, the resulting dough is retained at 20 to 40° C. for about 20 minutes to 10 hours, for a first fermentation to prepare a sponge dough. Secondary raw materials including water, salt, sugars, oil, and skim milk are added to and kneaded with the sponge dough to prepare bread dough. If necessary, the dough is left to rest for several hours for fermentation, and then, the resulting dough is divided in portions of suitable quantities, which are then left to rest for fermentation at 20 to 40° C. for a given period of time, for the purpose of the formation of a network structure of wheat gluten. After the fermentation, the portions are charged in baking molds, for proofing. Satisfactorily, the proofing period is a term of approximately 40 minutes to 12 hours in total. After the termination of fermentation, the dough is baked in an oven at 180 to 250° C. Even after long-term storage, the loaf of baked bread can retain excellent texture, compared with loaves of bread from general wheat flour types.

According to conventional methods except for the substitution of conventional wheat flour with the modified wheat flour of the present invention, pastas such as spaghetti and macaroni and noodles such as Japanese noodles (udon and soba) and Chinese noodles (including the sheets of gyoza and wang-tong), can be prepared. For the preparation of Chinese noodles, for example, the modified wheat flour and an aqueous solution of alkaline salts (kansul) are kneaded together to prepare dough; the dough is then left to stand at a preset temperature (aging process), followed by sheeting, combining and rolling; and the resulting dough is finally cut into pieces of a desired length and a desired width to be thus prepared as fresh Chinese noodle. The boiled Chinese noodle recovered by boiling the fresh noodle are with preferable hardness, good bite, and preferable elasticity; in other words, the resulting boiled Chinese noodle is resilient with resistance to the teeth, additionally with excellent noodle color and appearance.

Hereinafter, the method for modifying fish paste and the method for producing fish-paste processed products is described.

The treatment method with TG and oxidoreductase is exemplified by a method by means of the enzyme preparation of the present invention containing TG and oxidoreductase as the essential structural components thereof.

A process of adding the enzyme preparation comprises, for example, adding the enzyme preparation to fish after a leaching process for producing a fish paste. The other process comprises adding the enzyme preparation of the present invention to frozen fish meat as a raw material for producing a fish-paste product. By any of these methods, the gelation potency and color of general fish pastes can be modified and improved.

Herein, TG and the oxidoreductase are used at amounts of about 0.01 to 200 units and about 0.01 to 200 units, respectively, per gram of the protein in the fish paste to be used.

For producing a fish paste by the addition of the enzyme preparation, raw fish materials including sea-water fish such as Alaska pollack and nibe croaker (guchi; of the Family Sciaenidae) and fresh-water fish such as carp and sogyo (of the family carp), are used and subjected to meat recovery, leaching and dewatering processes, to recover dewatered fish. To the dewatered fish are added protein denaturing-preventive agents such as phosphate salts, and sugars and the enzyme preparation of the present invention according to the treatment method with TG and oxidoreductase. Then, a fish paste can be prepared.

During the process of producing fish-paste products, the enzyme preparation of the present invention is added to raw material fish pastes prepared from those sea-water fish and fresh-water fish, according to the treatment method with TG and oxidoreductase; and then, the resulting mixtures are subjected to cutting, setting, molding, heating and cooling processes, to prepare fish-paste products.

The resulting products are crisp to the teeth, and have elasticity and smoothness. From raw materials of sea-water fish pastes and fresh-water fish pastes prepared after landing, are prepared fish-paste products with such texture and additionally with modified color.

Pickles generally comprising components of 2.5 to 4.5% of salt, 1 to 3% of sugar, 0.5 to 1.2% of polyphosphate salts, 0.04 to 0.05% of nitrite salts, 0.08 to 0.25% of sodium absorbate and 5 to 15% of extraneous proteins (as a combination of plural proteins), in the form of a pickle solution, may be used for processing poultry and cattle meats. The components excluding the extraneous proteins do not differ so much, depending on the manufacturer, but each manufacturer has an absolutely unique technique how to make a combination of extraneous proteins. The combination of the extraneous proteins is of significance because the combination determines the quality of the resulting final products. Generally, the concentration of soybean protein and egg white as the extraneous proteins is about 2.5 to 6% in a pickle solution; and the concentration of caseins and whey protein is about 1 to 5% therein. When added to the pickle, TG disadvantageously causes the increase of viscosity; even when TG is contained in the enzyme preparation of the present invention according to the treatment method with TG and oxidoreductase, however, no increase of viscosity can be observed, under no influence of the combination of extraneous proteins or the concentration thereof. Thus, the final products such as ham, roasted pork and bacon prepared by injecting the pickle containing the enzyme preparation of the present invention into fresh meat are excellent in terms of smooth texture during swallowing and color.

In this case, TG and the oxidoreductase are used at amounts of about 1 to 1,000 units, preferably about 5 to 500 units and about 1 to 1,000 units, preferably about 5 to 500 units, respectively, per 100 g of solid in the pickle.

At least one of a substrate of the oxidoreductase, a protein partial hydrolysate, milk protein and a thiol group-containing material may be used at about 0.01 to 50 g, preferably about 0.05 to 30 g per of solid in the pickle.

According to well-known methods, the enzyme-containing pickle of the present invention may be used for treating poultry and cattle meats at an appropriately selected amount, depending on the amounts of the enzymes required for the treatment of the amount of a protein to be treated.

The modification method of soybean protein according to the present invention is described below.

For example, water is added to defatted soybean, to extract the protein and remove the debris (okara); then, the resulting protein extract solution is recovered. The extract solution adjusted to pH 4.5 is subjected to isoelectric precipitation, followed by whey discarding to recover protein curd. Water is added to the curd, followed by neutralization, to recover a protein slurry. To the protein slurry is added the enzyme preparation of the present invention for enzymatic reaction, according to the treatment method with TG and oxidoreductase; subsequently, the resulting mixture is sterilized under heating and dried, whereby a soybean protein powder can be recovered. Soybean-processed products prepared by using the soybean protein, such as soybean curd, were excellent in view of texture, flavor and color.

Then, TG and oxidoreductase are used at amounts of about 0.01 to 200 units and about 0.01 to 200 units, respectively, per gram of the protein to be used.

The method for binding together foods, particularly poultry and cattle meats and cut fish pieces, is now described. According to the treatment method with TG and oxidoreductase, more specifically, bound food products with neat bound area could be recovered by dissolving the enzyme preparation of the present invention in water, coating the resulting solution on the binding area of a fresh steak meat piece or a cut fish piece thinly, shaping the resulting piece and subsequently retaining the piece at ambient temperature or a low temperature.

TG and oxidoreductase are used in this case at amounts of about 0.01 to 200 units and about 0.01 to 200 units, respectively, per gram of the protein to be used.

In accordance with the invention, the modification of raw food materials such as wheat flour, fish paste, poultry and cattle meats and soybean protein, as well as the industrial-scale production of processed food products such as wheat processed products, fish processed products and processed products from poultry and cattle meats, can be carried out with no specific difficulty, according to general production methods, except for the addition of the enzyme preparation of the present invention. No novel procedure or process is additionally required for general production methods.

The applicable range of the combination of TG and oxidoreductase in accordance with the invention is not limited only to the modification of raw food materials and processed food products. The processing with the combination of the two enzymes, for example the enzyme preparation of the present invention, is effectively applicable to targeted protein containing materials. The target materials include for example milk processed products such as ice cream and yogurt, sweets such as pudding, egg curd (in a shape of soybean curd prepared a from egg), jelly and mousse.

Having generally described the invention, a further understanding can be obtained by reference to specific examples which are provided herein for the purposes of illustration only and are not intended to be limiting unless otherwise specified.

EXAMPLES

Example 1

Production of Enzyme Preparation 1

A composition was mixed together, comprising 100 g of TG (TG with a specific activity of 1,000 units/g; manufactured by Ajinomoto, Co.; derived from a microorganism *Streptoverticillium mobaraence*), 100 g of glucose oxidase (Hyderase 15 with a specific activity of 1500 units/g; manufactured by Amano Pharmaceuticals Co.) and 800 g of a wheat protein partial hydrolysate (Glutamine Peptide with a mean molecular weight of about 7,000; manufactured by DMV Japan, Co. The resulting mixture was filled and packed in a package material of an oxygen-impermeable 5-layer laminate film comprising a linear low-density polyethylene layer of 70 μm, a polyethylene layer of 15 μm, an aluminum foil of 9 μm, a polyethylene layer of 15 μm and a polyethylene terephthalate layer of 12 μm, starting from the utmost inner layer, to prepare an enzyme preparation for foods.

Example 2

Production of Wheat Flour

By removing small stone pieces and iron pieces and the like from a raw material Canadian wheat of 5 kg (Dark Northern Spring species at a water content of 11.8% and a protein content of 14.5%), the wheat was purified and placed in a tank, to which was then added water to a final water content of about 14.5% in the wheat. Then, the resulting wheat mixture was left to stand at 25° C. for 24 hours. The enzyme preparation for foods as prepared in Example 1 was dissolved, at a ratio of 1.45 g per kg—wheat, in water to be added for tempering. The resulting solution was spray added to the resulting wheat mixture so that the solution could be dispersed therein homogeneously. In this case, TG, glucose oxidase and the wheat protein partial hydrolysate were added at their quantities corresponding to 1.0 unit, 1.5 units and 0.013 g, respectively.

After tempering, coarse albumen grains were recovered by separating wheat shell from the mixture (disruption process). Then, shell debris contaminated therein was removed through a combination of sieving and air selection (purification process). Furthermore, coarse purified grains were ground by means of a smooth roll and were then sieved and fractionated, depending on the size of the resulting powder, to recover six fractions (grinding process). From the six fractions was recovered a 60% flour as a general wheat flour sample (the product of the invention; a raw food material).

At the tempering process, additionally, wheat flour was recovered in absolutely the same manner as for the product of the invention, except for the use of an enzyme preparation containing only TG as the enzyme preparation of the present invention for foods (TG used at the same amount as the amount for the product of the invention) (Comparative Example 1). Otherwise, wheat flour was recovered in absolutely the same manner as for the product of the invention, except for no use of any enzyme preparation (Comparative Example 2).

Example 3

Production of Chinese Noodles

By using the three types of wheat flour thus recovered, Chinese noodles and loaves of bread were prepared and evaluated.

2,000 g of each of the wheat flour types (the product of the invention, and Comparative Examples 1 and 2) was weighed, with which were blended salt of 20 g, alkaline salts (kansui) of 20 g and water of 800 g; and the resulting mixture was kneaded together at 500 mmHg by means of a vacuum mixer. Subsequently, the resulting kneaded material was subjected to sheeting with a noodle machine (manufactured by Shinagawa Noodle Machine Kabushiki Kaisha), followed by two series of combining and four series of rolling. The resulting rolled dough was cut in a fresh Chinese noodle shape. Six expert panelists conducted the organoleptic assessment of the resulting Chinese noodle on the basis of 10-score grades while the control product (Comparative Example 2) was ranked as point 5. The assessment results are shown in Table 1.

Herein, the assessment results of flavor and color are shown with the following symbols;

⊚: very good;

○: good;

Δ: normal.

TABLE 1

| Sample | Elasticity | Glutinousness | General score of texture | Comment | Flavor | Color |
| --- | --- | --- | --- | --- | --- | --- |
| Product of the invention | 7.7 | 8.2 | 8.0 | Glutinous and good biting with very good smoothness during swallowing | ⊚ | ⊚ |
| Comparative Example 1 | 7.9 | 7.5 | 7.7 | noodle quality slightly better than general (Comparative Example 2) | Δ | Δ |
| Comparative Example 2 | 5.0 | 5.0 | 5.0 | general noodle quality | Δ | Δ |

As apparent from the results in Table 1, the product of-the invention is excellent, in terms of physico-chemical properties-and texture and additionally in terms of flavor and color.

Example 4

Production of Loaves of Bread

Using the modified wheat flour produced in Example 2 as the product of the invention and wheat flour of two types in Comparative Examples 1 and 2, loaves of bread were prepared and then evaluated. 1,400 g of each wheat flour type was weighed, to which were added 40 g of yeast, 2.5 g of yeast food and 750 g of water; the resulting mixture was then mixed together at a low speed for 2 minutes, a medium speed for 4 minute and a high speed f or one minute, by means of a Hobart mixer. Subsequently, a processed oil of 50 g was added to the resulting mixture, which was then mixed together at a medium speed for 3 minutes and a high speed for one minute. The mixture was then subjected to a first fermentation by letting the resulting dough rest under conditions of 27° C. and 75% RH for 4 hours, to prepare a sponge dough. The dough at the termination of the first fermentation was at a temperature of 128° C. and pH 5.4. Into the sponge dough were kneaded 40 g of salt, 60 g of sugar, 60 g of glucose, 60 g of shortening, 40 g of skim milk and 440 g of water, and the resulting mixture was kneaded together with a mixer, to prepare bread dough. The bread dough was left to stand at 28° C. for about 10 minutes (second fermentation) and was then divided and rounded in six equal portions. The resulting pieces were left to stand at 28° C. for another 10 minutes (third fermentation) and were then filled in a baking mold. The mold was left to stand under conditions of 37° C. and 75% RH for 50 minutes, for another fermentation (fourth fermentation). Subsequently, the fermented bread dough was placed in an oven and baked therein at 220° C. for 40 minutes, to prepare loaves of bread.

Assessment of Loaves of Bread

Each loaf of bread thus prepared was sliced into a thickness of 1.5 cm and subjected to organoleptic assessment by 10 expert panelists. Compared with those from Comparative Example 1 and 2, the loaf of bread from the product of the invention was very excellent in terms of the color and quality of the surface crust, porosity (sudachi), the tissue and color of the inner phase, and crispness to the teeth.

Example 5

Modification of Egg White

According to general methods, an egg white powder was prepared. More specifically, a raw material fresh egg after inspection and washing was cracked in aseptic environment by means of an automatic egg cracker arranged on an egg yolk separator, to recover fresh egg white. To a solution of the fresh egg white were added yeast extract at about 0.1%, bread an yeast (*Saccharomyces cerevigiae*) at about 0.2% and the enzyme preparation recovered in Example 1 at 0.5%, for 5-hr fermentation. Per g of protein in the egg white, TG, glucose oxidase and the wheat protein partial hydrolysate were added at their quantities corresponding to 5 units, 7.5 units and 0.04 g, respectively, whereby sugar was removed therefrom. Subsequently, the resulting mixture was subjected to fermentation and filtration, to remove unnecessary matters from the mixture. The egg white solutions lightly acidic was sprayed at a pressure of 1500 to 1600 lb/inch into dry air at 80 to 90 ° C., to prepare an egg white powder (the product of the invention). As a control product, an egg white powder was prepared under the same conditions, except for no addition of the enzyme preparation.

The resulting two types of the egg white powders were subjected to the assessment of their gelation potencies of the heated gel therefrom and the appearance of the resulting gels. As to the gelation potencies, a 4-fold volume of water was added to each egg white powder, and the resulting solution was heated at 85° C. for preparing a gel; and the gel strength was measured.

The results of the assessment are shown in Table 2.

TABLE 2

| Sample | Gel strength (kg/cm$^2$) | Gel deformation ratio (%) | Appearance, etc. |
|---|---|---|---|
| Product of the invention | 2.18 | 52 | whitish color, high visco-elastically, mild taste and flavor, compared with control product properties of general egg white powder |
| Control product | 1.40 | 30 | |

As apparent from the results in Table 2, the product of the invention is more excellent with a higher gel strength and a higher gel deformation ratio.

Example 6

Production of Enzyme Preparation 2

A composition was homogeneously mixed together rapidly, comprising 100 g of TG (TG with a specific activity of 1,000 units/g; manufactured by Ajinomoto, Co.; derived from a microorganism *Streptoverticillium mobaraence*), 100 g of glucose oxidase (Hyderase 15 with a specific activity of 1500 units/g; manufactured by Amano Pharmaceuticals Co.), 200 g of a wheat protein partial hydrolysate (Glutamine Peptide with a mean molecular weight of about 7,000; manufactured by DMV Japan, Co.), 200 g of glucose and 400 g of dextrin. The resulting mixture was filled and packed in a package material of an oxygen-impermeable 5-layer laminate film composition comprising a linear low-density polyethylene layer of 70 μm, a polyethylene layer of 15 μm, an aluminum foil of 9 μm, a polyethylene layer of 15 μm and a polyethylene terephthalate layer of 12 μm, starting from the utmost inner layer, to prepare an enzyme preparation for foods.

Example 7

Production of Fish Cake 1

To a mixture of 500 g of grade-SA Alaska pollack preliminarily cracked as it was at a frozen state into a flake form and 500 g of a fish paste prepared after landing were added 30 g of salt and 600 g of ice water, and the resulting mixture was mixed together with a Stephan cutter. Subsequently, the following materials were added to the resulting mixture: 50 g of potato starch, 50 g of sugar, 20 g of a sweet sake (mirin), 10 g of powdered seasoning, and 2.0 g of the enzyme preparation recovered in Example 6. The resulting mixture was agitated with a Stephan cutter at a temperature of 8° C. or less inside the mixture. TG, glucose oxidase and the wheat protein partial hydrolysate were added at their quantities corresponding to 1.0 unit, 1.5 units and 0.02 g, respectively. The mixture was filled in a casing tube and rest therein under heating at 40° C. for 30 minutes, and then, the resulting mixture was heated at 90° C. for 30 minutes followed by cooling, to prepare a fish cake. As a control, a fish cake (Comparative Example 3) was prepared by the same method, except for the use of an enzyme preparation containing only TG as the enzyme preparation (TG at the same amount as that for the product of the invention). A fish cake (Comparative Example 4) was also prepared by the same-method, except for no use of any enzyme preparation.

Assessment of these Fish Cakes

The resulting three types of fish cakes were subjected to the organoleptic assessment by six expert panelists on the basis of 10-score grades while the control product (Comparative Example 4) was ranked as point 5. The assessment results are shown in Table 3.

Herein, the assessment results of flavor and color are shown with the following symbols;

⊚: very good;

○: good;

Δ: normal.

TABLE 3

| Sample | Elasticity | Glutinousness | General score of texture | Comment | Flavor | Color |
|---|---|---|---|---|---|---|
| Product of the invention | 8.1 | 7.0 | 8.0 | flexible and good biting with very good smoothness; excellent color and flavor | ⊚ | ⊚ |

TABLE 3-continued

| Sample | Elasticity | Glutinousness | General score of texture | Comment | Flavor | Color |
|---|---|---|---|---|---|---|
| Comparative Example 3 | 8.5 | 5.2 | 7.0 | hard, not flexible, with elasticity; dark color and poor taste | Δ | Δ |
| Comparative Example 4 | 5.0 | 5.0 | 5.0 | soft with no biting; dark color and poor taste | Δ | Δ |

As apparently shown from the results in Table 3, the fish cake from the product of the invention is extremely great in terms of clear color with no darkness, good bite with enhanced resilience and smoothness during swallowing, regarding texture.

Example 8

Production of Fish Cake 2

A fish cake was prepared by the same treatment using 1000 g of the paste of a fresh-water fish carp. The fish cake was subjected to general gel strength testing methods. Consequently, the jelly strength was 453 g-cm in case of the 44 fish cake (the product of the invention) with addition of the enzyme preparation of the present invention as recovered in Example 6; 300 g-cm in case of the fish cake with no addition of any enzyme preparation; and 385 g-cm in case of the fish cake (Comparative Example 4) produced by using an enzyme preparation containing only TG as the enzyme preparation. The jelly strength of the product of the invention was 1.5-fold and 1.3-fold the jelly strengths of the fish cake with no addition of any enzyme preparation and the fish cake produced by using the enzyme preparation containing only TG, respectively. The results of the organoleptic assessment thereof by six expert panelists indicate that the product of the invention had good biting along with strong elasticity and with particularly preferable taste and flavor and color.

Example 9

Production of Soybean Protein

A 9-fold volume of water was added to defatted soybean. The mixture at pH 6.5 was adjusted to pH 7.0 by the addition of sodium hydroxide, followed by agitation at 40° C. for 30 minutes, to extract the protein. From the extract was removed the debris by means of a super decanter, to recover a soybean extract solution. The soybean extract solution was adjusted to pH 4.5 by using sulfuric acid, for isoelectric precipitation of the protein, from which whey was removed by means of a super decanter, to prepare protein curd (at a solid content of 32%).

A 8-fold volume of water was added to the curd after drying, for cracking the curd by means of a disperse mill to prepare a protein slurry, which was then neutralized with sodium hydroxide. 0.3 part of the enzyme preparation recovered in Example 5 was added to and mixed with 100 parts of the neutralized protein slurry, for enzyme reaction at 50° for 20 minutes. TG, glucose oxidase and the wheat protein partial hydrolysate were added at their quantities corresponding to 9.0 unit, 13.6 units and 0.02 g, respectively, per g-protein in soybean. Into the enzyme reaction solution was ejected high-temperature steam through a mixing tube similar to ejector, thereby heating the enzyme reaction solution at 120° C. for 60 seconds, and the resulting enzyme reaction solution was ejected into a cyclone retained at a reduced pressure of about 600 mmHg, to rapidly cool the solution. By subsequently spray drying the solution at an inlet temperature of 160° C. and an outlet temperature of 80° C., a soybean protein powder (the product of the invention) was recovered. A soybean protein powder (Comparative Example 5) was recovered by the same method, except for the use of an enzyme preparation containing only TG (at the same amount as for the product of the invention) among the enzyme preparation of the present inventions recovered in Example 6. A soybean protein powder (Comparative Example 6) was recovered by the same method, except for no use of the enzyme preparation of the present inventions recovered in Example 6.

Gels were prepared from the soybean protein powders and assessed according to general gel strength testing methods and by the measurement of the L (lightness) value by means of a chromaticity meter. The results of the assessment are shown in Table 4.

TABLE 4

| Sample | Gel strength | Color | Comment |
|---|---|---|---|
| Product of the invention | 989 | 58 | White and transparent with weak soybean odor or flavor, compared with control products |
| Comparative Example 5 | 750 | 40 | dark and strong soybean odor and flavor |
| Comparative Example 6 | 638 | 40 | very dark with strong soybean odor and flavor |

As apparent from the results in Table 4, the product of the invention exerts excellent physico-chemical properties with transparency in white color and with the improvement in soybean odor and flavor.

Furthermore, the functions of the resulting soybean protein powders (the product of the invention and Comparative Examples 5 and 6) were assessed by using the system for fish cake.

Example 10

Production of Fish Cake 3

To 1,000 g of frozen grade-SA Alaska pollack were added 30 g of salt and 600 g of ice water, and the resulting mixture was agitated with a Stephan cutter. Subsequently, the following materials were added to the resulting mixture; 50 g of potato starch, 50 g of sugar, 20 g of a sweet sake (mirin), 10 g of powdered seasoning, and 50 g each of the three types of soybean protein powders recovered in Example 9. The resulting mixtures were agitated with a Stephan cutter under controls so that the temperature might be 8° C. or less. The resulting fish pastes were filled and rest in a casing tube at 40° C. for 40 minutes, followed by heating at 90° C. for 30 minutes and subsequent cooling, to prepare a fish cake. The results of the organoleptic assessment apparently indicate that the fish cake with addition of the soybean protein powder as the product of the invention exerted enhanced elasticity and great smoothness, with preferable color and flavor, compared with the fish cake with addition of the soybean protein powder of Comparative Example 5 or 6.

Example 11

Production of Enzyme Preparation 3

A composition was mixed together, comprising 100 g of TG (TG with a specific activity of 1,000 units/g; manufactured by Ajinomoto, Co.; derived from a microorganism *Strentoverticillium mobaraence*), 100 g of glucose oxidase (Hyderase 15 with a specific activity of 1500 units/g; manufactured by Amano Pharmaceuticals Co.), 100 g of a wheat protein partial hydrolysate (Glutamine Peptide with a mean molecular weight of about 7,000; manufactured by DMV Japan, Co.), 100 g of yeast extract (Yeast Extract YE-KM; manufactured by Kojin Kabushiki Kaisha), 100 g of glucose, an oligosaccharide (Isomalto 900-P; manufactured by Showa Industry, Co. Ltd.) and 300 g of corn starch. The resulting mixture was filled and packed in a package material of an oxygen-impermeable 5-layer laminate film comprising a linear low-density polyethylene layer of 70 $\mu$m, a polyethylene layer of 15 $\mu$m, an aluminum foil of 9 $\mu$m, a polyethylene layer of 15 $\mu$m and a polyethylene terephthalate layer of 12 $\mu$m, starting from the utmost inner layer, to prepare an enzyme preparation.

Example 12

Production of Pickle Solution

A pickle solution was prepared, by mixing together and dissolving together a composition comprising salt at 3.6%, sugar at 2.4%, sodium L-glutamate at 0.5%, sodium nitrite at 0.05%, sodium absorbate at 0.19%, sodium polyphosphate at 0.72%, extraneous proteins including isolated soybean protein (Ajipron HS2 ; manufactured by Ajinomoto, Co.) at 5%, egg white (Egg White Powder; manufactured by Taiyo Chemical, Co. Ltd. at 5%, sodium casemate (Miprodan; manufactured by Nissei Kyoeki Kabushiki Kaisha) at 2%, and whey protein (Sunlact N; manufactured by Taiyo Chemical Co. Ltd.) at 1%, the enzyme preparation recovered in Example 11 at 0.13% and water at 79.41%. Herein, TG, glucose oxidase, the partially hydrolyzed wheat protein product, sodium casemate and yeast extract were added at their amounts corresponding to 63 units, 95 units, 0.063 g, 10 g and 0.063 g, respectively, per 100 g of solid in the pickle.

Example 13

Production of Boneless Ham

According to a general method, a boneless ham block was prepared, using pork ham as the raw material. The pickle solution was injected at 60% as a ratio to the raw material meat, for a tumbling process at 5° C. overnight. Casing was conducted as follows; drying at 60° C. for 2 hours, smoking at the same temperature for one hour and steam boiling at 75° C. for 2 hours were effected in a fibrous casing of a folding width of 11 cm. As control products, alternatively, boneless ham blocks were prepared under the same conditions, except for the use of an enzyme preparation containing only TG (at the same amount as for the product of the invention) (Comparative Example 7) and for no use of any enzyme preparation (Comparative Example 8).
Assessment of Ham Blocks The resulting boneless ham blocks were assessed in an organoleptic manner by ten expert panelists. The boneless ham block with no addition of the enzyme preparation as the product of the invention was so dry with not any cohesiveness. Alternatively, the boneless ham block with addition of the enzyme preparation of the present invention as recovered In Example 11 exerted excellent cohesiveness and appropriate elasticity, with preferable physico-chemical properties and texture with excellent smoothness during swallowing. Furthermore, the ham block with addition of the enzyme preparation of the present invention apparently did not split when sliced into a 2-mm thickness, so the ham block was at a high product yield.

The ham block prepared by using the enzyme preparation containing only TG was hard with resistance to teeth, like fish cake, so the ham block was inferior to the product of the invention.

Example 14

Production of Enzyme Preparation 4

A composition was mixed together, comprising 50 g of TG (TG with a specific activity of 1,000 units/g; manufactured by Ajinomoto, Co.; derived from a microorganism *Streptoverticillium mobaraence*), 50 g of glucose oxidase (Hyderase 15 with a specific activity of 1500 units/g; manufactured by Amano Pharmaceuticals Co.), 50 g of a wheat protein partial hydrolysate (Glutamine Peptide with a mean molecular weight of about 7,000; manufactured by DMV Japan, Co.), 400 g of sodium casemate (Miprodan; manufactured by Nissei Kyoeki Kabushiki Kaisha), 200 g of an oligosaccharide (Isomalto 900-P; manufactured by Showa Industry, Co. Ltd.) and 250 g of corn starch. The resulting mixture was filled and packed in a package material of an oxygen-impermeable 5-layer laminate film comprising a linear low-density polyethylene layer of 70 $\mu$m, a polyethylene layer of 15 $\mu$m, an aluminum foil of 9 $\mu$m, a polyethylene layer of 15 $\mu$m and a polyethylene terephthalate layer of 12 $\mu$m, starting from the utmost inner layer, to prepare an enzyme preparation.

Example 15

Production of Bound Food

To small pork ham pieces (meat pieces in squares of about 2 to 5 cm) weighed 1000 g in total was added a solution of 10 g of the enzyme preparation in Example 14 in 30 g of water, followed by uniform mixing with a kneader. Herein, TG, glucose oxidase, the wheat protein partial hydrolysate and sodium caseinate were added to their amounts corresponding to 2.5 units, 3.8 units, 0.0025 g and 0.02 g, respectively, per g-meat protein. After mixing, the resulting mixture was filled in a casing tube of a folding width of 75 mm, and was then left to stand overnight in a refrigerator. The bound meat block was peeled off from the casing and was sliced into pieces of about 9-mm thickness, to prepare a bound meat block (the product of the invention). As a control product, a bound meat block (control product) was prepared under absolutely the same conditions, except for the use of an enzyme preparation containing only TG and sodium caseinate at the same individual amounts as described above.

The resulting individual bound meat blocks were subjected to organoleptic assessment as they were fresh or after heating on a frying pan. The product of the invention exerted high binding strength, compared with the control product; the appearance and color of the product of the invention were so excellent that the bound area could totally never be identified.

Example 16

Production of Enzyme Preparation 5

A composition was mixed together, comprising 50 g of TG (TG with a specific activity of 1,000 units/g; manufactured by Ajinomoto, Co.; derived from a microorganism *Streptoverticillium mobaraence*), 50 g of absorbate oxidase (Absorbate oxidase powder with a specific activity of 1000 units/g; manufactured by Amano Pharmaceuticals Co.), 250 g of sodium absorbate (manufactured by Dai-ichi Pharmaceuticals Co.), and 650 g of lactose. The resulting mixture was filled and packed in a package material of an oxygen-impermeable 5-layer laminate film comprising a linear low-density polyethylene layer of 70 µm, a polyethylene layer of 15 µm, an aluminum foil of 9 µm, a polyethylene layer of 15 µm and a polyethylene terephthalate layer of 12 µm, starting from the utmost inner layer, to prepare enzyme preparation 5.

Example 17

Production of Enzyme Preparation 6

A composition was mixed together, comprising 50 g of TG (TG with a specific activity of 1,000 units/g; derived from a microorganism *Streptoverticillium mobaraence*) and 950 g of lactose. The resulting mixture was filled and packed in the same package material of the 5 -layer laminate film as in Example 16, to prepare enzyme preparation 6, which was used as a control product.

Example 18

Production of Japanese Noodle (Udon)

To a type of flour for udon (Suzume; manufactured by Nisshin Seif un Co. Ltd.) of 1000 g and 430 g of water with addition of salt of 30 g was added the enzyme preparation 5 at 1% of flour weight (the product of the invention), or the enzyme preparation 6 at 1% of flour weight (control product 2), or no enzyme preparation (control product 1). These products were individually subjected to sheeting once, combining once and rolling three times, to prepare udon noodles by using a cutting roll #12.

The prepared udon noodles were boiled during a preset period of 12 minutes. Based on 10-score grades with score 5 assigned to the control product 1, organoleptic assessment regarding the items of elasticity, glutinousness and overall, was executed by ten expert Panelists. As shown in Table 5, consequently, the control product 2 has strong elasticity but with no glutinousness, and with hard and fragile touch; the product of the invention udon is endowed with strong elasticity at high glutinousness and fairly balanced preferable texture with smoothness and still retains the firmness, with no occurrence of softening for a long term even after boiling.

TABLE 5

| Sample | Amount | Elasticity | Glutinousness | Overall |
|---|---|---|---|---|
| Control 1 | no addition | 5.0 | 5.0 | 5.0 |
| Control 2 | enzyme preparation 6 at 1% | 6.5 | 4 | 6.0 |
| Product of the invention | enzyme preparation 5 at 1% | 8.5 | 7.0 | 8.0 |

Example 19

Production of Japanese Noodle Soba (Buckwheat Noodles)

Using the same enzyme preparations as in Example 18, Japanese noodle soba and loaves of bread were prepared and evaluated.

400 g of backwheat flour (Betsuheiwa; manufactured by Hokuto Seifun Co. Ltd.) and 600 g of hard-wheat flour (Seikei; manufactured by Nisshin Seifun Co. Ltd.) were mixed together, and to the resulting mixture were added water of 400 g and salt of 30 g. To a control product 1 was never added any enzyme preparation; to a control product 2 and an product of the invention were added the enzyme preparations 6 and 5, respectively, each at 1% of flour weight; the resulting mixtures were individually mixed together by means of a mixer at 95 rpm for 7 minutes. The mixture were subjected to sheeting with a noodles machine; manufactured by Shinagawa Noodle Machine Co., and the resulting three types of dough were subjected to combining once and rolling three times to prepare noodles, which were then cut with a cutting roll #24, to prepare three types of Japanese noodle soba.

These types of soba were boiled in water for 2.5 minutes and were then subjected to the organoleptic assessment of their elasticity, glutinousness and overall by ten expert panelists on the basis of 10-grade ranking with point 5 assigned to the control product 1 with no addition. As shown in Table 6, the control product 1 was with texture with weak elasticity at low glutinousness; the control product 2 was with texture with strong elasticity but was fragile; the product of the invention Japanese noodle soba exerted elasticity with good bite and with preferable texture in good balance with glutinousness.

◎: very good;
○: good;
∆: normal.

TABLE 6

| Sample | Amount Added | Elasticity | Glutinousness | Overall | Comment |
|---|---|---|---|---|---|
| Control product 1 | no addition | 5.0 | 5.0 | 5.0 | general noodle quality |
| Control product 2 | enzyme preparation 6 at 1% | 6.0 | 3.8 | 6.2 | Elasticity with low glutinousness; hard and fragile texture |
| Product of the invention | enzyme preparation 5 at 1% | 8.3 | 7.5 | 8.2 | good bite with good balance between elasticity and glutinousness and with preferable texture |

As shown from the results in Table 6, the product of the invention is very excellent in terms of physico-chemical properties and texture and additionally in terms of flavor and color.

Example 20

Production of Loaves of Bread

Loaves of bread prepared by using the enzyme preparations produced in Examples 16 and 17 as the product of the invention and the control 2, respectively, were assessed along with a loaf of bread with no enzyme addition as control product 1. 1400 g of hard-wheat flour was weighed, to which were added the individual enzyme preparation at 0.2% of flour weight, 40 g of yeast, 2.5 g of yeast food and 750 g of water; the resulting mixture was,then mixed together at a low speed for 2 minutes, a medium speed for 4 minute and a high speed for one minute by means of a Hobart mixer. Subsequently, a processed oil of 50 g was added to the resulting mixture, which was then mixed together at a medium speed for 3 minutes and a high speed for one minute. The mixture was then subjected to a first fermentation by letting the resulting mixture rest under conditions of 27° C. and 75% RH for 4 hours, to prepare a sponge dough. Into the sponge dough were kneaded 40 g of salt, 60 g of sugar, 60 g of glucose, 60 g of shortening, 40 g of skim milk and 440 g of water, and the resulting mixture was kneaded together with a mixer to prepare bread dough. The bread dough was left to stand at 28° C. for about 10 minutes (second fermentation) and was then divided and rounded in six equal portions. The resulting pieces were left to stand at 28° C. for another 10 minutes (third fermentation) and were then filled in a baking mold. The mold was left to stand under conditions of 37° C. and 75% RH for 50 minutes, for another fermentation (fourth fermentation). Subsequently, the fermented bread dough pieces were placed in an oven and baked therein at 220° C. for 40 minutes, to prepare loaves of bread.

Assessment of Loaves of Bread

Each loaf of bread thus prepared was sliced into a thickness of 1.5 cm and subjected to organoleptic assessment by ten expert panelists. Compared with those from the control products 1 and 2, the load of bread from the product of the invention (the enzyme preparation 5 of Example 16) exerted very excellent physico-chemical properties and had texture in terms of the color and quality of the surface crust, porosity, the tissue and color of the inner layer, and crispness to the teeth.

Example 21

Production of Pasta

Pasta types prepared by using the enzyme preparations 5 & 6 produced in Examples 16 and 17 as the product of the invention and the control 2, respectively, were assessed, along with a pasta type with not any enzyme addition as control product 1. 1000 g of durum semolina flour was weighed, to which were added the individual enzyme preparations at 1% of flour weight. To the resulting mixtures was added 300 g of water, followed by mixing with a pasta machine (Type PM 50; manufactured by Lucky Caffee Machine Co.) for 10 minutes. The resulting mixtures were immediately subjected to extrusion molding through a nozzle with a dice of 1.8-mm diameter, to prepare spaghetti pieces cut into a length of 30 cm.

The prepared spaghetti pieces were boiled for 8 minutes, and were then mixed with a sauce. Organoleptic assessment was executed by ten expert panelists. Based on 10-score grades with point 5 assigned to the control product 1 with no enzyme addition, the organoleptic assessment thereof in terms of the items of elasticity, glutinousness and overall was executed by ten expert panelists. As shown in Table 7, consequently, a spaghetti product with preferable texture and aldente touch was recovered, with good bite and smoothness demanded for pasta and with a hard core part but smooth surface.

TABLE 7

| | | Organoleptic Assessment | | | |
|---|---|---|---|---|---|
| Sample | Amount | Elasticity | Glutinousness | Overall | Comment |
| Control 1 | no addition | 5.0 | 5.0 | 5.0 | general noodle quality |
| Control 2 | enzyme preparation 6 at 1% | 7.0 | 4.7 | 6.8 | strong elasticity; hard, readily breakable with poor smoothness during swallowing |
| Product of the invention | enzyme preparation 5 at 1% | 8.8 | 7.5 | 8.5 | good bite with good balance between elasticity and glutinousness |

As shown in Table 7, the product of the invention is very excellent in terms of physico-chemical properties and preferable texture and additionally in terms of flavor and color.

ADVANTAGES OF THE INVENTION

Foods containing a protein treated with transglutaminase (TG) and oxidoreductase, preferably additionally treated in the presence of at least one of the following: a substrate of the oxidoreductase, a protein partial hydrolysate, milk protein and a thiol group-containing material, can produce the effect of the TG action on the improvement of physico-chemical properties and can additionally provide excellent properties and good texture, such as smoothness during swallowing and good bite, with preferable color and flavor.

For example, such excellent properties as described above can be imparted to food materials such as fish pastes (from fresh-water fish, in particular), poultry and cattle meats, soybean protein and egg white. Various processed food products such as wheat processed products, fish-paste products, and processed food products of poultry and cattle meats, which are prepared by using these food materials, can procure preferable properties such as smoothness during swallowing and good bite, in addition to the effect of TG on the improvement of physico-chemical properties; still additionally, the processed food products can get superior flavor and color.

The method for producing such excellent protein-modified food products and the enzyme preparation for use in the protein modification are also provided.

Obviously, numerous modifications and variations of the present invention are possible in light of the above teachings. It is therefore to be understood that within the scope of the appended claims, the invention may be practiced otherwise than as specifically described.

This application is based on Japanese Patent Application Ser. No. 10-161094, filed on Jun. 9, 1998, and incorporated herein by reference in its entirety.

What is claimed is:

1. A method of preparing a food, comprising incorporating a protein treated with at least one transglutaminase and at least one oxidoreductase into the food, wherein the food is selected from the group consisting of pastas, noodles, egg white, fish-paste products, and meat products.

2. A method of preparing a food, comprising contacting a food containing a protein with at least one transglutaminase and at least one oxidoreductase wherein the food is selected from the group consisting of pastas, noodles, egg white, fish-paste products, and meat products.

3. A method of preparing a food, comprising:

contacting a protein with at least one transglutaminase and at least one oxidoreductase, followed by incorporating the protein into a food wherein the food is selected from the group consisting of pastas, noodles, egg white, fish-paste products, and meat products.

4. The method of preparing a food according to claim 1, wherein the food is pasta.

5. The method of preparing a food according to claim 1, wherein the food is noodles.

6. The method of preparing a food according to claim 1, wherein the food is egg white.

7. The method of preparing a food according to claim 1, wherein the food is a fish-paste product.

8. The method of preparing a food according to claim 1, wherein the food is a meat product.

9. The method of preparing a food according to claim 2, wherein the food is pasta.

10. The method of preparing a food according to claim 2, wherein the food is noodles.

11. The method of preparing a food according to claim 2, wherein the food is egg white.

12. The method of preparing a food according to claim 2, wherein the food is a fish-paste product.

13. The method of preparing a food according to claim 2, wherein the food is a meat product.

14. The method of preparing a food according to claim 3, wherein the food is pasta.

15. The method of preparing a food according to claim 3, wherein the food is noodles.

16. The method of preparing a food according to claim 3, wherein the food is egg white.

17. The method of preparing a food according to claim 3, wherein the food is a fish-paste product.

18. The method of preparing a food according to claim 3, wherein the food is a meat product.

* * * * *

UNITED STATES PATENT AND TRADEMARK OFFICE
CERTIFICATE OF CORRECTION

PATENT NO.   : 6,383,533 B1
DATED        : May 7, 2002
INVENTOR(S)  : Soeda et al.

It is certified that error appears in the above-identified patent and that said Letters Patent is hereby corrected as shown below:

Column 6,
Line 33, "for the- treatment" should read -- for the treatment --.

Column 9,
Line 66, "material rob" should read -- material --.

Column 10,
Line 11, "readily break" should read -- readily breakable --.

Column 11,
Line 65, "the is remaining other" should read -- the remaining other --.

Column 14,
Line 55, "prepared a from" should read -- prepared from --.

Column 16,
Line 35, "product of-the" should read -- product of the --;
Line 37, "properties-and texture" should read -- properties and texture --;
Line 50, "4 minute" should read -- 4 minutes --; and
"speed f or" should read -- speed for --.

Signed and Sealed this

Fourth Day of February, 2003

JAMES E. ROGAN
*Director of the United States Patent and Trademark Office*